United States Patent
Baik et al.

(10) Patent No.: US 9,334,228 B2
(45) Date of Patent: May 10, 2016

(54) METHOD FOR PREPARING DIALKYL CARBONATE

(71) Applicant: RESEARCH INSTITUTE OF INDUSTRIAL SCIENCE & TECHNOLOGY, Pohang (KR)

(72) Inventors: Joon Hyun Baik, Pohang-si (KR); Jae Cheon Koh, Pohang-si (KR); Kyong Tae Kim, Pohang-si (KR); Dong Jun Koh, Pohang-si (KR); Young Sam Sa, Pohang-si (KR); Yun Min Kim, Daejeon (KR); Chul Ung Kim, Daejeon (KR)

(73) Assignee: RESEARCH INSTITUTE OF INDUSTRIAL SCIENCE & TECHNOLOGY, Pohang (KR)

( * ) Notice: Subject to any disclaimer, the term of this patent is extended or adjusted under 35 U.S.C. 154(b) by 244 days.

(21) Appl. No.: 14/057,111

(22) Filed: Oct. 18, 2013

(65) Prior Publication Data

US 2014/0051880 A1 Feb. 20, 2014

Related U.S. Application Data

(63) Continuation of application No. PCT/KR2012/003070, filed on Apr. 20, 2012.

(30) Foreign Application Priority Data

Apr. 20, 2011 (KR) ........................ 10-2011-0036777

(51) Int. Cl.
*C07C 68/00* (2006.01)

(52) U.S. Cl.
CPC .............. *C07C 68/00* (2013.01); *Y02P 20/582* (2015.11)

(58) Field of Classification Search
None
See application file for complete search history.

(56) References Cited

U.S. PATENT DOCUMENTS

| 5,534,649 | A | 7/1996 | Cho |
| 6,010,976 | A | 1/2000 | Ryu |
| 7,271,120 | B2 | 9/2007 | Sun |
| 2010/0312001 | A1 | 12/2010 | Wershofen |

FOREIGN PATENT DOCUMENTS

| CN | 1597096 | 3/2005 |
| CN | 101417229 | 4/2009 |
| JP | 57-026645 A | 2/1982 |
| KR | 10-2011-0012957 | 2/2011 |
| WO | 95/17369 | 6/1995 |
| WO | 2011013880 | 2/2011 |

OTHER PUBLICATIONS

European Patent Office, European Search Report dated Aug. 25, 2014, of the corresponding European Patent Application No. 12774514.9.
Dengfeng Wang, et al., "Synthesis of dimethyl carbonate from methyl carbamate and methanol over lanthanum compounds", Fuel Processing Technology, Sep. 2010, 91(9), 1081-1086.
Database CAPLUS, accession No. 2010:328838 & Dengfang Wang, et al., Shiyou Huagong, Feb. 2010, 3(2), 141-145.
Hong Wang et al., "Highly selective synthesis of dimethyl carbonate from urea and methanol catalyzed by ionic liquids", Fuel Processing Technology vol. 90, pp. 1198-1201. (Oct. 2009).
Kim, Yun Min, et al., "Study on composition of dimethyl carbonate from two step reaction of metal oxide catalyst", Annual Spring Meeting of The Korean Society of Industrial and Engineering Chemistry, (Apr. 15, 2009).
S. Bowden and E. Butler, "Intermolecular forces in liquid systems. Part I. The physical properties of the alkyl carbonates", J. Chem. Soc., pp. 75-78 (Oct. 1939).
Peter Ball, Heinz Füllmann, and Walter Heintz, "Carbonates and Polycarbonates from Urea and Alcohol", Angew. Chem. Int. Ed. Engl. vol. 19, No. 9, pp. 718-720 (Sep. 1980).
Yoshio Ono, "Dimethyl carbonate for environmentally benign reaction", Pure & Appl. Chem., vol. 68, No. 2, pp. 367-375 (Mar. 1996).

*Primary Examiner* — Rebecca Anderson
*Assistant Examiner* — Po-Chih Chen
(74) *Attorney, Agent, or Firm* — Lex IP Meister, PLLC

(57) ABSTRACT

Disclosed is a method for preparing a dialkyl carbonate, in which a dialkyl carbonate such as dimethyl carbonate is economically prepared in an environmentally-friendly manner at a higher yield while reducing generation of a by-product. The method for preparing the dialkyl carbonate includes reacting urea, an alkyl carbamate having 1 to 3 carbon atoms, or a mixture thereof with a monovalent alcohol having 1 to 3 carbon atoms in the presence of a room temperature ionic liquid and a catalyst including a salt of a transition metal or a rare earth metal.

18 Claims, 4 Drawing Sheets

METHOD FOR PREPARING DIALKYL CARBONATE

CROSS-REFERENCE TO RELATED APPLICATION

This application is a continuation application of International Application No. PCT/KR2012/003070 filed on Apr. 20, 2012, which claims priority to and the benefit of Korean Patent Application No. 10-2011-0036777 filed on Apr. 20, 2011, the entire contents of which are incorporated herein by reference.

BACKGROUND OF THE INVENTION (a) Field of the Invention

The present invention relates to a method for preparing a dialkyl carbonate. More particularly, the present invention relates to a method for preparing a dialkyl carbonate in which a dialkyl carbonate such as dimethyl carbonate is economically prepared in an environmentally friendly manner at a higher yield while reducing generation of a by-product.

(b) Description of the Related Art

Dimethyl carbonate (DMC) as a representative dialkyl carbonate material is colorless and odorless, and has an environmentally friendly molecular structure without toxicity to a human body. Further, since dimethyl carbonate has various chemical reactivities, a reactive group such as a methyl, methoxy, or methoxycarbonyl group may be introduced. Dimethyl carbonate may replace highly toxic and corrosive chemicals such as dimethyl sulfate or methyl halides by introducing the reactive group. In addition, dimethyl carbonate has high solubility and may therefore be used as an environmentally friendly solvent to replace a solvent such as chlorobenzene. Recently, dimethyl carbonate has been used as a substitute material for phosgene as a raw material of polycarbonate, an additive for improving an octane number for vehicles, or an electrolyte solution of a rechargeable battery.

Dimethyl carbonate has been typically prepared with an alcohol such as methanol, phosgene, and a highly concentrated sodium hydroxide solution. However, it is known that there are many problems in views of safety and the environment due to toxic phosgene and the highly concentrated sodium hydroxide solution.

Another method for preparing dimethyl carbonate is an EniChem process. The EniChem process is a method for preparing dimethyl carbonate by oxidizing carbon monoxide and methanol using a monovalent copper chloride catalyst with oxygen in the air. However, the EniChem process has problems in that toxic carbon monoxide is used as a raw material, a conversion rate is low, and a cost of energy used to purify and circulate unreacted methanol is high due to generation of water as a by-product. Further, there are problems in that, since the monovalent copper chloride catalyst is readily oxidized into divalent copper ions, catalytic activity is reduced, and supplementation of a reaction device against corrosion and handling of explosion are required. Moreover, there is a problem in that, due to the presence of a small amount of chloride ions in products, a refining cost is rapidly increased when dimethyl carbonate is used as an electrolyte solution.

Still another method for preparing dimethyl carbonate is an Ube process in which methanol is oxidized into nitrogen dioxide to prepare methyl nitrate, water is removed, methyl nitrate reacts with carbon monoxide in the presence of a platinum catalyst to prepare dimethyl carbonate, nitrogen oxide comes into contact with air to again be converted into nitrogen dioxide, and nitrogen dioxide is circulated. The Ube process has problems in that, although a cost of energy for separation and purification is relatively low, the use of the highly toxic and corrosive carbon monoxide and nitrogen oxide requires an anti-corrosion reaction device, an anti-explosion safety device, and a precise concentration controlling device, and there is a risk of leakage of reactants.

Yet another method for preparing dimethyl carbonate is a Texaco process in which ethylene oxide (or propylene oxide) and carbon dioxide are reacted with each other at high pressure in the presence of a catalyst to prepare ethylene carbonate (or propylene carbonate), and then prepare dimethyl carbonate and ethylene glycol (or propylene glycol) through an ester exchange reaction with methanol. The Texaco process does not use carbon monoxide and thus has excellent safety as compared to the EniChem process and the Ube process. However, since the process is performed at high temperature and pressure, there is a risk of explosion due to leakage of ethylene oxide used as a raw material. Further, although the ester exchange reaction is performed at a high temperature, a conversion rate is not high, and thus there is a problem in that a large amount of energy is used to separate and purify unreacted materials as well as dimethyl carbonate and ethylene glycol as products.

Recently, a method for preparing dimethyl carbonate by directly reacting urea and methanol in the presence of a catalyst has been actively studied. In this method, inexpensive urea is used as a raw material, and since water as a by-product is not produced, a ternary azeotropic mixture such as methanol-water-dimethyl carbonate is not produced, and separation and purification processes may be easily carried out. Further, ammonia produced as the by-product may be reacted with carbon dioxide to be converted into urea and reused, and thus it is possible to prepare dimethyl carbonate by a further environmentally-friendly process.

As described above, the known methods for preparing dimethyl carbonate using urea and methanol are as follows. (1) a method for reacting urea and methanol in the presence of a zinc acetate catalyst (S. Bowden and E. Buther, J. Chem. Soc. 1939, Vol. 78), and (2) a method for synthesizing dialkyl carbonate by reacting urea, a primary aliphatic alcohol such as methanol, an organic metal compound, and a catalyst of a phosphine-based organic material (Peter Ball, Heinz Fullmann, and Walter Heintz, "Carbonates and Polycarbonates from Urea and Alcohol", Angew. Chem. Int. Ed. Engl. 1980, Vol. 19, No. 9, pp 718-720; WO 95/17369). However, in these methods, it is difficult to synthesize a dialkyl carbonate such as dimethyl carbonate at a sufficient yield.

Further, a (3) method for preparing a dialkyl carbonate by using a catalyst of an organotin-based compound and a high boiling point electron donor compound, such as a polyglycol ether compound, as a co-catalyst (J. Yong Ryu, U.S. Pat. No. 6,010,976) is known, and various process patents are known based on the method (3). However, the aforementioned method has a drawback in that, since the catalyst of the organotin-based compound is unstable to water, activity thereof is reduced by water included in a raw material as an impurity, and also has a problem of toxicity. Further, the polyglycol ether compound used as the co-catalyst may be decomposed or polymerized at high temperatures, and thus activity thereof as the co-catalyst may be reduced due to an occurrence of a change in viscosity or carbonization. Moreover, it is difficult to regenerate the catalyst and the co-catalyst, which may cause an environmental pollution.

Meanwhile, a method (4) for preparing dimethyl carbonate by using a catalyst in which transition metal oxides such as Zn, Pb, Mn, La, or Ce and alkali (earth) metal oxides such as K, Na, Cs, Li, Ca, or Mg are impregnated in alumina or silica, and directly reacting urea and methanol using a reactor or a distillation column is disclosed in U.S. Pat. No. 7,271,120 B2. In this method, the catalyst and reactants may be easily separated. However, a reaction temperature at which dimethyl carbonate is synthesized is much higher than a boiling point of methanol, it is necessary to maintain a vapor-liquid equilibrium state at high pressure, and if produced ammonia and dimethyl carbonate are not discharged, a reaction yield may be reduced. Moreover, by-products such as N-methylmethyl carbamate (N-MMC) or N,N-dimethylmethyl carbamate may be formed due to a side reaction between methyl carbamate (MC) as an intermediate product and dimethyl carbonate.

As described above, in the method for preparing dimethyl carbonate through reaction distillation, in order to improve the reaction yield and distillation efficiency of dimethyl carbonate at the reaction temperature that is higher than the boiling point of methanol and the high vapor pressure of methanol, it is necessary to maintain the temperature and the pressure at which the vapor-liquid equilibrium is obtained, discharge ammonia, and obtain a distillate. In this case, the obtained distillate is an azeotropic mixture of dimethyl carbonate and methanol, and the concentration of dimethyl carbonate as the product may be reduced due to the azeotropic mixture at high pressure, which reduces productivity. Further, in this preparation method, by-products such as N-MMC or N,N-dimethylmethyl carbamate formed by reaction of methyl carbamate (MC) as the intermediate product may be produced in a large amount due to high reactivity of synthesized dimethyl carbonate (Yoshio Ono, "Dimethyl carbonate for environmentally benign reaction", Pure & Appl. Chem., 1996, Vol. 68, No. 2, pp 367-375).

In addition, in (5) U.S. Pat. No. 5,534,649, urea or alkyl carbamate and alkyl alcohol are reacted in the presence of a quaternary ammonium salt-based ionic liquid such as tetramethylammonium hydrogen carbonate methyl ester or tetramethylammonium carbamate and an organotin-based catalyst to prepare a dialkyl carbonate. However, there is a problem in that a maximum yield of a dimethyl carbonate is 4.13%, which is very low.

Because of the aforementioned problems, a method of preparing a dialkyl carbonate such as dimethyl carbonate having various industrial purposes in an environmentally friendly manner at a higher yield while reducing generation of a by-product is continuously required.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a method for preparing a dialkyl carbonate, in which the dialkyl carbonate is economically prepared in an environmentally friendly manner at a higher yield while reducing generation of a by-product.

An exemplary embodiment of the present invention provides a method for preparing a dialkyl carbonate. The method includes reacting urea, an alkyl carbamate having 1 to 3 carbon atoms, or a mixture thereof with a monovalent alcohol having 1 to 3 carbon atoms in the presence of a room temperature ionic liquid and a catalyst including a salt of a transition metal or a rare earth metal.

In the method for preparing a dialkyl carbonate, the salt of the transition metal may be a salt of a transition metal of Group III or IV, and the salt of a transition metal or a rare earth metal of the catalyst may be a salt of Zr, Ce, La, or Y. Further, the salt of the transition metal or the rare earth metal may be a nitrate or halide of the corresponding metal.

As a more specific example, the catalyst may be a salt of a transition metal or a rare earth metal of $ZrO(NO_3)_2$, $Ce(NO_3)_3$, $CeCl_3$, $ZrCl_4$, $La(NO_3)_3$, or $LaCl_3$.

Further, in the method for preparing a dialkyl carbonate, the room temperature ionic liquid may be a room temperature ionic liquid including a cation that is capable of generating a hydrogen ion ($H^+$) and a hydrophobic anion including fluorine. In this case, the cation may be a quaternary ammonium-based cation, an imidazolium-based cation, an N-hydroxyalkylpyridium-based cation, a pyrazolium-based cation, a pyrrolinium-based cation, a quaternary phosphonium-based cation, a thiazolium-based cation, or a sulfonium-based cation having an alkyl group or a hydroxyalkyl group. The anion may be a bis(trifluoromethylsulfonyl)imide anion, a trifluoromethanesulfonate anion, or a tris(trifluoromethylsulfonyl)methanide anion.

As a more specific example, the room temperature ionic liquid may be [Choline][NTf2] (ionic liquid in which (β-hydroxyethyl)trimethylammonium$^+$ and bis(trifluoromethylsulfonyl)imide$^-$ are bonded).

Meanwhile, in the method for preparing a dialkyl carbonate, the reacting may be carried out at a temperature of 130 to 300° C. and a pressure of 0.1 to 15 atm, and appropriately at about atmospheric pressure.

Further, in the reacting, the urea, the alkyl carbamate, or the mixture thereof, and the monovalent alcohol, may be used at a molar ratio of 1:1 to 1:100. The catalyst and the room temperature ionic liquid may be used at a weight ratio of 1:1 to 1:1000.

In addition, in the method for preparing a dialkyl carbonate, the reacting of the urea, the alkyl carbamate, or the mixture thereof with the monovalent alcohol may include a first reaction of reacting the urea, the alkyl carbamate having 1 to 3 carbon atoms, or the mixture thereof with the monovalent alcohol having 1 to 3 carbon atoms in the presence of the room temperature ionic liquid and the catalyst, and a second reaction of further reacting a product of the first reaction to convert isocyanic acid included in the product of the first reaction into alkyl carbamate. In this case, the first reaction may be carried out in a stirred reactor, and the second reaction may be carried out in a fixed-bed reactor. The fixed-bed reactor may be filled with Raschig rings or a formed body in which a metal oxide catalyst is impregnated. Further, the second reaction may be carried out with addition of the catalyst including oxides of one or more metals selected from the group consisting of Zr, Ce, Zn, Ti, Pb, and Mg.

Meanwhile, the method for preparing a dialkyl carbonate may further include, after the reacting of the urea, the alkyl carbamate, or the mixture thereof with the monovalent alcohol as reactants, separating a product including dialkyl carbonate, a by-product including ammonia, and an unreacted residue including monovalent alcohol and alkyl carbamate from a product of the reacting. In this case, the unreacted residue including the monovalent alcohol and the alkyl carbamate may be circulated into the reaction and reused. The by-product including ammonia may be removed.

According to the exemplary embodiment, the separating may include: primarily distilling the product of the reaction in a first distillation column to circulate the unreacted residue of a column bottom into the reaction and purifying the by-product at a column top to form a first product including ammonia, monovalent alcohol, and dialkyl carbonate; deaerating and purifying ammonia remaining in the first product to form a second product including monovalent alcohol and dialkyl carbonate; secondarily distilling the second product in a second distillation column to circulate the unreacted residue of the column bottom into the reaction and form a third product including monovalent alcohol and dialkyl carbonate at the column top; membrane separating the third product in a membrane separation device to further separate the unreacted residue to circulate the unreacted residue into the second distillation column and form a fourth product including dialkyl carbonate at a concentration that is higher than the concentration of the third product; and tertiarily distilling the fourth product in a third distillation column to circulate a distillate of the column top into the membrane separation device and recover a final product including dialkyl carbonate at the column bottom. In this case, the first to third distillation columns may be atmospheric distillation columns, and the membrane separation device may be a pervaporation device.

According to the exemplary embodiment of the present invention, a dialkyl carbonate can be economically prepared in an environmentally-friendly manner at a higher yield by using a room temperature ionic liquid and a catalyst in a predetermined metal salt form. In the preparation method, since the room temperature ionic liquid has excellent stability to water, air, or a temperature change, and a low vapor pressure at high temperatures, the room temperature ionic liquid is hardly consumed during the reaction, and can well-dissolve the urea or the alkyl carbamate as a reactant. Further, decomposition or sublimation of the reactant at high temperatures can be suppressed. Accordingly, since a catalytic action in a metal salt form can be promoted even at atmospheric pressure and generation of a by-product can be suppressed to improve productivity by using the room temperature ionic liquid as a reaction medium, use of energy can be significantly reduced, and since waste materials are not generated, the method is environmentally friendly. Moreover, it is possible to increase product concentration at an azeotropic point by performing distillation under a reaction condition of a low pressure, and it is possible to reduce devices and improve productivity by reducing an amount of alcohol as a circulated raw material. Furthermore, a reuse ratio of the room temperature ionic liquid and the catalyst is high, and a yield of dialkyl carbonate can be significantly improved.

In addition, it is possible to further improve a lifespan of the catalyst and prepare a dialkyl carbonate at a further improved yield by using the catalyst in a predetermined metal salt form.

Eventually, according to the present invention, it is possible to economically prepare a dialkyl carbonate having various industrial availabilities in an environmentally friendly manner at a higher yield.

DETAILED DESCRIPTION OF THE EMBODIMENTS

Figure 1:
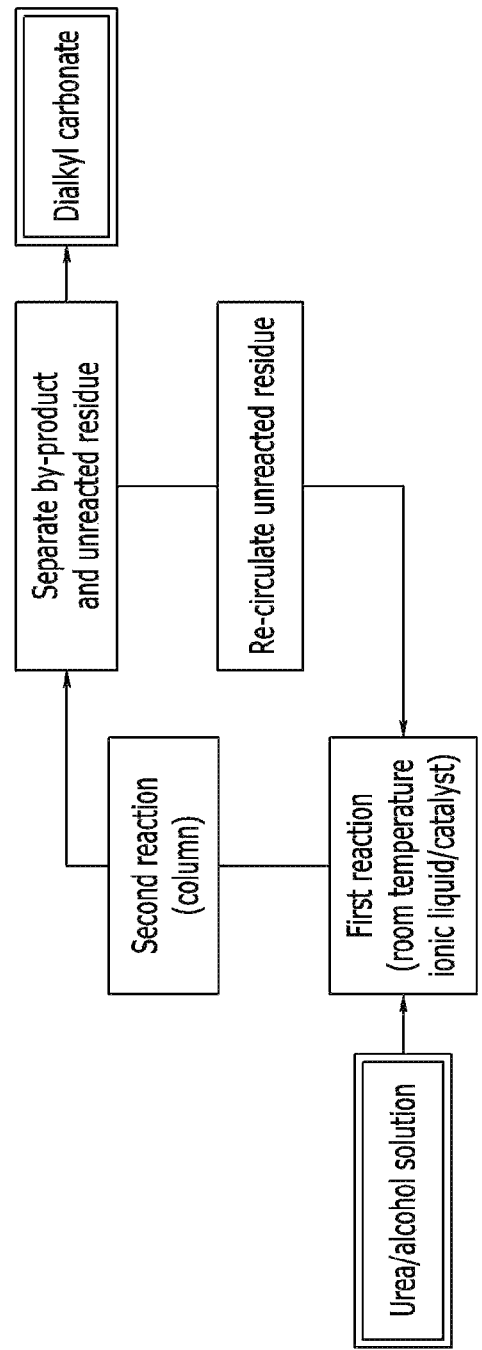
FIG. 1 is a block diagram schematically showing a method for preparing a dialkyl carbonate according to an exemplary embodiment of the invention.

Hereinafter, a method of preparing a dialkyl carbonate according to a specific exemplary embodiment of the invention will be described.

According to the exemplary embodiment of the invention, a method for preparing a dialkyl carbonate, including reacting urea, an alkyl carbamate having 1 to 3 carbon atoms, or a mixture thereof with a monovalent alcohol having 1 to 3 carbon atoms in the presence of a room temperature ionic liquid and a catalyst including a salt of a transition metal or rare earth metal is provided.

In the preparation method, the room temperature ionic liquid is used as a reaction medium and the catalyst in a predetermined metal salt form is used to apply urea and a monovalent alcohol such as methanol, thus preparing a dialkyl carbonate such as dimethyl carbonate. As described above, a dialkyl carbonate may be prepared at a higher yield and a higher reaction speed based on the following principle by using the room temperature ionic liquid as the reaction medium.

Typically, a main reaction scheme of reacting alcohol and urea or an alkyl carbamate to prepare a dialkyl carbonate is equivalent to the following Reaction Scheme 1.

<Reaction Scheme 1>

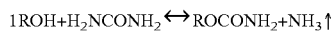

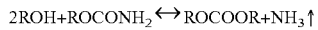

That is, when urea and alcohol are reacted, an alkyl carbamate may be formed, and the alkyl carbamate may be reacted back with alcohol to prepare a dialkyl carbonate. Further, in each reaction, ammonia may be generated as a by-product. Accordingly, when the dialkyl carbonate and ammonia generated during the reaction are efficiently discharged, an equilibrium reaction is performed in a positive direction, and thus reaction speed and yield may be improved. However, since alcohol (e.g., methanol) used as a reactant during the reaction has a relatively low boiling point, the reaction pressure typically needs to be increased in order to maintain a reaction temperature, and solubility of generated ammonia and dimethyl carbonate is increased due to the high pressure. Therefore, an equilibrium constant Ke of Reaction Scheme 1 may be reduced, which may cause a reduction in yield and reaction speed. Moreover, generation of sub-reactants such as N-alkylalkyl carbamate, N,N-dialkylalkyl carbamate, trialkylamine, dialkylamine, or monoalkylamine may be increased.

However, in the preparation method of the exemplary embodiment, a drawback according to high pressure may be solved by using the room temperature ionic liquid as a reaction medium. The room temperature ionic liquid is not reacted with alcohol used as the reactant, and may act as a heating medium for heating alcohol to the reaction temperature. Further, since the room temperature ionic liquid has excellent stability to water, air, or a temperature change and a low vapor pressure at high temperatures, the room temperature ionic liquid is hardly consumed during the reaction step, and may well-dissolve urea or alkyl carbamate as the reactant. Moreover, decomposition or sublimation of the reactant at high temperatures may be suppressed.

However, according to Korean Registered Patent No. 1102537 by the present inventors, a method for reacting urea and alcohol using a catalyst of an oxide form of a transition metal or a rare earth metal together with the room temperature ionic liquid to prepare dialkyl carbonate is known. According to this method, it was confirmed that the catalyst was deactivated and activity or lifespan of the catalyst was largely reduced during the reaction step in which the room temperature ionic liquid and the metal oxide catalyst were stirred. Accordingly, there were confirmed problems in that the yield of dialkyl carbonate was reduced according to a reaction time and the use amount of the catalyst was largely increased.

The present inventors have continuously studied, resulting in the confirmation that the problems of the prior art can be completely solved by using the catalyst in a salt form of a transition metal or a rare earth metal. In this case, the term "salt of a transition metal or a rare earth metal" or "metal salt" may be understood to also include hydrates of the salts. Further, the term "metal salt" may refer to an ionic bonded salt in a form where cations of a transition metal or a rare earth metal are bonded to anions. In addition, the catalyst in the metal salt form may be homogeneously dissolved in the room temperature ionic liquid to form an organic metal complex compound.

As supported through the following examples, it was confirmed that the catalyst could be homogeneously dissolved in the room temperature ionic liquid as the reaction medium to largely improve activity and lifespan, and a dialkyl carbonate could be prepared at an excellent yield over a long period of time by using the catalyst in the metal salt form. Moreover, it was found that the catalyst could be homogeneously dissolved in the room temperature ionic liquid as the reaction medium to provide excellent activity and operation by an interaction with the reaction medium even at low pressure conforming to atmospheric pressure. Therefore, in the preparation method of the exemplary embodiment, an increase in generation of the sub-reactant due to an increase in reaction pressure does not substantially occur, and a dialkyl carbonate may be efficiently prepared at a further improved yield and reaction speed. Moreover, according to the preparation method of the exemplary embodiment, the catalyst can be used over a long period of time, generation of the by-product or the sub-reactant can be reduced, a reuse ratio of an unreacted residue can be increased, and thus a dialkyl carbonate can be prepared in a further environmentally friendly manner.

Hereinafter, the method for preparing a dialkyl carbonate according to the exemplary embodiment will be described in more detail for each step.

In the reaction step of urea, an alkyl carbamate having 1 to 3 carbon atoms, or a mixture thereof with a monovalent alcohol having 1 to 3 carbon atoms, a solution of urea dissolved in the monovalent alcohol may be injected into a reaction solution including the catalyst and the room temperature ionic liquid to carry out the reaction. In this case, after the alkyl carbamate having 1 to 3 carbon atoms is dissolved instead of urea or together with urea in the monovalent alcohol, the solution may be injected into the reaction solution to carry out the reaction. In the specific example, the reaction step may be carried out by dissolving and stirring the catalyst in the metal salt form in the room temperature ionic liquid, maintaining a predetermined reaction temperature, and injecting the alcohol solution in which urea, the alkyl carbamate, or the mixture thereof is dissolved at a predetermined flow rate.

In this case, since the alcohol and alkyl carbamate do not cause steric hindrance, it is easy to perform the reaction to dialkyl carbonate. Since a boiling point of a generated dialkyl carbonate is lower than the reaction temperature, the dialkyl carbonate may be recovered in a gas phase.

Further, in the reaction step, the monovalent alcohol having 1 to 3 carbon atoms such as methanol, ethanol, or n-propyl alcohol may be used as the alcohol. An alkyl carbamate having 1 to 3 carbon atoms such as methyl carbamate, ethyl carbamate, or n-propyl carbamate may be used as the alkyl carbamate. A dialkyl carbonate such as dimethyl carbonate, diethyl carbonate, or di-n-propyl carbonate may be prepared by using these reactants.

In addition, the reaction step may be carried out at a temperature of about 130 to 300° C., about 140 to 250° C., or about 150 to 200° C., and a pressure of about 0.1 to 15 atm, about 0.3 to 10 atm, or about 0.5 to 5 atm, and appropriately at about atmospheric pressure. As described above, in the preparation method of the exemplary embodiment, the reaction step may be carried out at a relatively low pressure of around atmospheric pressure by using the room temperature ionic liquid as the reaction medium and using the catalyst in the metal salt form. As a result, as previously described above, generation of the sub-reactant may be reduced, and the dialkyl carbonate may be prepared at the high yield and reaction speed. However, the reaction step is not carried out only at about atmospheric pressure, and if necessary, the reaction step may be carried out while appropriately controlling reaction pressure by using a pressure control device.

Further, in the reaction step, urea, alkyl carbamate, or the mixture thereof and the monovalent alcohol may be used at a molar ratio of about 1:1 to 1:100, about 1:10 to 1:50, about 1:15 to 1:45, or about 1:15 to 1:40. The molar ratio may be controlled through control of the use amount of each reactant such as the urea or alcohol, or further controlled by a method for vaporizing alcohol. When the molar ratio is excessively low, the dialkyl carbonate may not be properly prepared or thermally decomposed by-products may be increased to reduce the yield. On the contrary, when the molar ratio is excessively high, a quantity of heat required in vaporization may be increased due to an excessive amount of alcohol to reduce heat efficiency.

In the example, urea, alkyl carbamate, or the mixture thereof may be used at a ratio at which the urea, alkyl carbamate, or the mixture thereof is maximally dissolved in alcohol to be saturated. For example, when urea and methanol are used, it is most preferable that the urea be dissolved and used at a ratio of about 18% at which urea is maximally dissolved in methanol at room temperature. However, since solubility of the urea to alcohol may depend on the temperature, an appropriate concentration of urea may be selected and used in consideration of the reaction temperature or the yield.

Meanwhile, in the reaction step, the room temperature ionic liquid is used as the reaction medium. The room temperature ionic liquid may refer to a material that is present in a liquid state at room temperature even though the room temperature ionic liquid is constituted by bonding of ions. As previously described above, the temperature required in the reaction may be maintained even though the reaction temperature is not increased by using the room temperature ionic liquid as the reaction medium. As a result, the dialkyl carbonate and ammonia may be efficiently continuously discharged to improve the yield and the reaction speed of the dialkyl carbonate.

A matter including a cation that is capable of generating hydrogen ions ($H^+$) and hydrophobic anions including fluorine may be used as the room temperature ionic liquid. As specific examples thereof, a room temperature ionic liquid including a quaternary ammonium-based cation, an imidazolium-based cation, a N-hydroxyalkylpyridium-based cation, a pyrazolium-based cation, a pyrrolinium-based cation, a quaternary phosphonium-based cation, a thiazolium-based cation, or a sulfonium-based cation having an alkyl group or a hydroxyalkyl group, and a bis(trifluoromethylsulfonyl)imide anion, a trifluoromethanesulfonate anion, or a tris(trifluoromethyl sulfonyl)methanide anion may be used.

While the catalyst in the metal salt form and the reactant such as urea and alkyl carbamate are efficiently dissolved by using the room temperature ionic liquid, sublimation of the reactants may be suppressed. Further, the reaction speed and the yield may be further improved due to an interaction with the catalyst. Moreover, the room temperature ionic liquid has hydrophobicity such that the room temperature ionic liquid is not substantially reacted with alcohol in the reactant, and may act as the heating medium for heating alcohol to the reaction temperature. Accordingly, when an appropriate room temperature ionic liquid is used, an appropriate reaction temperature may be obtained even though the reaction pressure is not substantially increased, and thus the yield and the reaction speed of the dialkyl carbonate may be further improved.

Additionally, since the room temperature ionic liquid basically has hydrophobicity and insolubility enabling separation from water to be easy, when performance of the catalyst is reduced or the catalyst is polluted, the metal salt catalyst dissolved therein may be removed through acid washing, and if necessary, the room temperature ionic liquid may be discolored by activated carbon and then washed with ether and distilled water to be reused. Accordingly, in the preparation method of the exemplary embodiment, since the catalyst and the reaction medium of the room temperature ionic liquid may be reused at a higher ratio, dialkyl carbonate may be prepared in an environmentally friendly manner.

Meanwhile, the most representative example of the room temperature ionic liquid may include [Choline][NTf2] ((β-hydroxyethyhtrimethylammonium$^+$.bis(trifluoromethylsulfonyl)imide$^-$). The room temperature ionic liquid may have unusual catalytic characteristics and solubility due to its structure and electromagnetic polarity. Further, since vapor pressure is very low even at high temperatures, there is no concern of a loss. Even though the room temperature ionic liquid is exposed to air and water, the room temperature ionic liquid is stable, and thus it is easy to handle the room temperature ionic liquid. Further, the room temperature ionic liquid is an environmentally-friendly liquid having hydrophobicity and insolubility to water and has excellent activity in the reaction of synthesizing dialkyl carbonate, and thus the room temperature ionic liquid may be appropriately used in the reaction step. Moreover, since the room temperature ionic liquid may suppress sublimation, vaporization, or decomposition of urea, and appropriately maintain urea or alkyl carbamate in a liquid phase at the reaction temperature, when the room temperature ionic liquid is used, the concentration of the reactant may be further increased to further improve reaction efficiency.

Meanwhile, in the reaction step, the catalyst in a predetermined metal salt form, which includes the salt of the transition metal or rare earth metal, is used. In this case, as described above, the scope of the term "salt of the transition metal or rare earth metal" or "metal salt" may be understood to also include hydrates of the salts. In the catalyst, the salt of transition metal may be a salt of a transition metal of Group III or IV. As more specific examples thereof, a salt of Zr, Ce, La, or Y may be used as the salt of the transition metal or rare earth metal, and nitrates or haloids of the transition metal or rare earth metal may be used. Some specific examples of the catalysts may include $ZrO(NO_3)_2$, $Ce(NO_3)_3$, $CeCl_3$, $ZrCl_4$, $La(NO_3)_3$, or $LaCl_3$, or predetermined hydrates thereof.

It was confirmed that the reaction step could be further promoted and dialkyl carbonate could be prepared at a higher yield by using the salt of the transition metal or rare earth metal of Group III or IV as the catalyst. Further, like the prior art as described above, when the catalyst in the oxide form of the transition metal or rare earth metal is used, the catalyst may be deactivated and activity or lifespan of the catalyst may be reduced during the reaction step wherein the room temperature ionic liquid and the catalyst are stirred. Accordingly, the yield of dialkyl carbonate may be reduced according to the reaction time to largely increase the use amount of the catalyst. On the other hand, in the exemplary embodiment, it was confirmed that the activity and the lifespan of the catalyst could be largely improved and a dialkyl carbonate could be prepared at an excellent yield over a long period of time by using the catalyst in the metal salt form, such as nitrates or haloids, that is capable of being homogeneously dissolved in the room temperature ionic liquid to form the organic metal complex compound.

Further, the catalyst may be used in an amount set so that a weight ratio of the catalyst to the room temperature ionic liquid is about 1:1 to 1:1000, about 1:3 to 1:500, or about 1:5 to 1:200. The reaction step may be further efficiently activated, and economic efficiency and an environmentally-friendly characteristic of the reaction step may be optimized by using the catalyst in the aforementioned content.

Meanwhile, in the method of preparing the dialkyl carbonate of the exemplary embodiment, as described above, after a first reaction step of reacting urea, the alkyl carbamate having 1 to 3 carbon atoms, or the mixture thereof with the monovalent alcohol having 1 to 3 carbon atoms in the presence of the room temperature ionic liquid and the catalyst is carried out, a second reaction step of further reacting a product of the first reaction step may be further carried out.

The second reaction step may be understood as a reaction step of converting an isocyanic acid included in the product of the first reaction step into an alkyl carbamate The conditions such as the temperature and the pressure of the second reaction step may conform to that of the first reaction step, and the second reaction step may be carried out in the same reactor as the first reaction step or in a separate reactor. However, in the second reaction step, in order to further promote a conversion reaction of the isocyanic acid, a metal oxide catalyst such as Zr, Ce, Zn, Ti, Pb, or Mg as will be described later may be further added, or the second reaction step may be carried out in a separate reactor including the aforementioned catalyst or may be carried out in a separate reactor where reaction conditions are partially controlled. The first reaction step and the second reaction step may be differentiated from each other by carrying out of the reaction step in the separate reactor and/or addition of the additional catalyst.

As shown in the following Reaction Scheme 2, at least a portion of urea or alkyl carbamate may be thermally decomposed while the first reaction step is carried out to form the isocyanic acid (HNCO).

<Reaction Scheme 2>

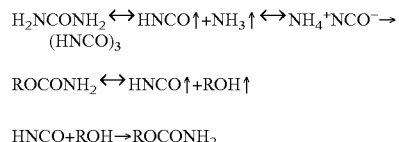

$ROCONH_2 \leftrightarrow HNCO\uparrow + ROH\uparrow$ $HNCO + ROH \rightarrow ROCONH_2$ However, the isocyanic acid may be reacted with ammonia to form ammonium isocyanate ($NH_4^+NCO^-$). Ammonium isocyanate may be precipitated in a solid phase in a cooler to be gradually converted into an ammonium cyanurate (($NH_4)_3(NCO)_3$) or cyanuric acid (($HNCO)_3$) compound having a 6-membered ring, which is not dissolved in alcohol. This may clog a path of the cooler to reduce cooling efficiency, and in severe cases, may become a cause of frequent replacement of the cooler.

In the second reaction step, the isocyanic acid may be reacted with alcohol to be converted into alkyl carbamate.

Problems according to ammonium cyanurate or the cyanuric acid may be minimized, generation of the sub-reactant such as methylamine may be further reduced, and the yield or purification efficiency of dialkyl carbonate may be further improved by carrying out the second reaction step.

Meanwhile, the second reaction step may be continuously carried out in the same reactor as the first reaction step, or the first reaction step may be carried out in the stirred reactor and the second reaction step may be carried out in a column-type fixed-bed reactor in order to further efficiently react and remove the isocyanic acid. Further, the metal oxide catalyst may be included in the fixed-bed reactor, and for example, the fixed-bed reactor may be filled with Raschig rings or a formed body in which the metal oxide catalyst is impregnated. In addition, in order to further efficiently carry out the second reaction step, for example, the reaction of converting the isocyanic acid, the second reaction step may be carried out with addition of the catalyst including oxides of one or more metals selected from the group consisting of Zr, Ce, Zn, Ti, Pb, and Mg. As described above, the reactor may be filled with the metal oxide catalyst.

In addition, for example, the reactants such as urea, alkyl carbamate, or the mixture thereof and alcohol may be supplied at a speed of about 0.1 to 5.0% V/W·min based on the room temperature ionic liquid to the reactor in which the first reaction step is carried out. However, the supply speed of the reactants may be variously controlled in consideration of a shape of the reactor or an amount of heat supplied to the reactor to maintain the reaction temperature.

Meanwhile, in the preparation method of the exemplary embodiment, after the reaction step is carried out, a step of separating the product including the dialkyl carbonate in the product of the reaction step from the by-product including ammonia and the unreacted residue including the monovalent alcohol and alkyl carbamate to finally obtain a product may be further carried out. FIG. 1 is a block diagram schematically showing a method for continuously preparing the dialkyl carbonate, which includes the separation step.

Referring to FIG. 1, after the first and second reaction steps are carried out, a step of separating the by-product and the unreacted residue from the products of the reaction steps may be carried out. That is, when each reaction step is carried out, the unreacted residue including unreacted alcohol and alkyl carbamate and ammonia as the by-product generated during the reaction step may be included together with the dialkyl carbonate as a final product in the product.

Accordingly, the dialkyl carbonate may be obtained with high purity by carrying out a step of distilling the unreacted residue and the by-product from the product of the reaction step using a distillation column or separating the unreacted residue and the by-product by a method such as membrane separation using a membrane separation device. Further, the unreacted residue including the alcohol and the alkyl carbamate, which is separated from the product, may be circulated (e.g., refluxed into the stirred reactor for the first reaction step) into the reaction step using a reboiler included in the distillation column and reused. The by-product including ammonia may be removed. In addition, the final product including the dialkyl carbonate, from which the unreacted residue and the by-product are removed, may be recovered and obtained with the high purity. Through the continuous preparation process, overall reaction efficiency may be further increased and the total generation amount of the by-product may be further reduced to prepare the dialkyl carbonate in an environmentally-friendly manner.

Meanwhile, until now, the case where after the first and second reaction steps are carried out, the separation step and/or the circulation and reuse steps are carried out is exemplified. However, of course, the second reaction step may be omitted and the separation step and/or the circulation and reuse steps may be carried out immediately after the reaction step corresponding to the first reaction step. Even in this case, dialkyl carbonate having the high purity may be obtained by removing the unreacted residue and the by-product from the product obtained through the reaction step, and the separated unreacted residue may be circulated by the reaction step (e.g., stirred reactor) or a reflux cooler connected to the stirred reactor and reused.

Further, the separation step and the circulation and reuse steps may be carried out together to continuously prepare the dialkyl carbonate. However, the dialkyl carbonate may be prepared in a batch form by carrying out only the separation step.

Figure 2:
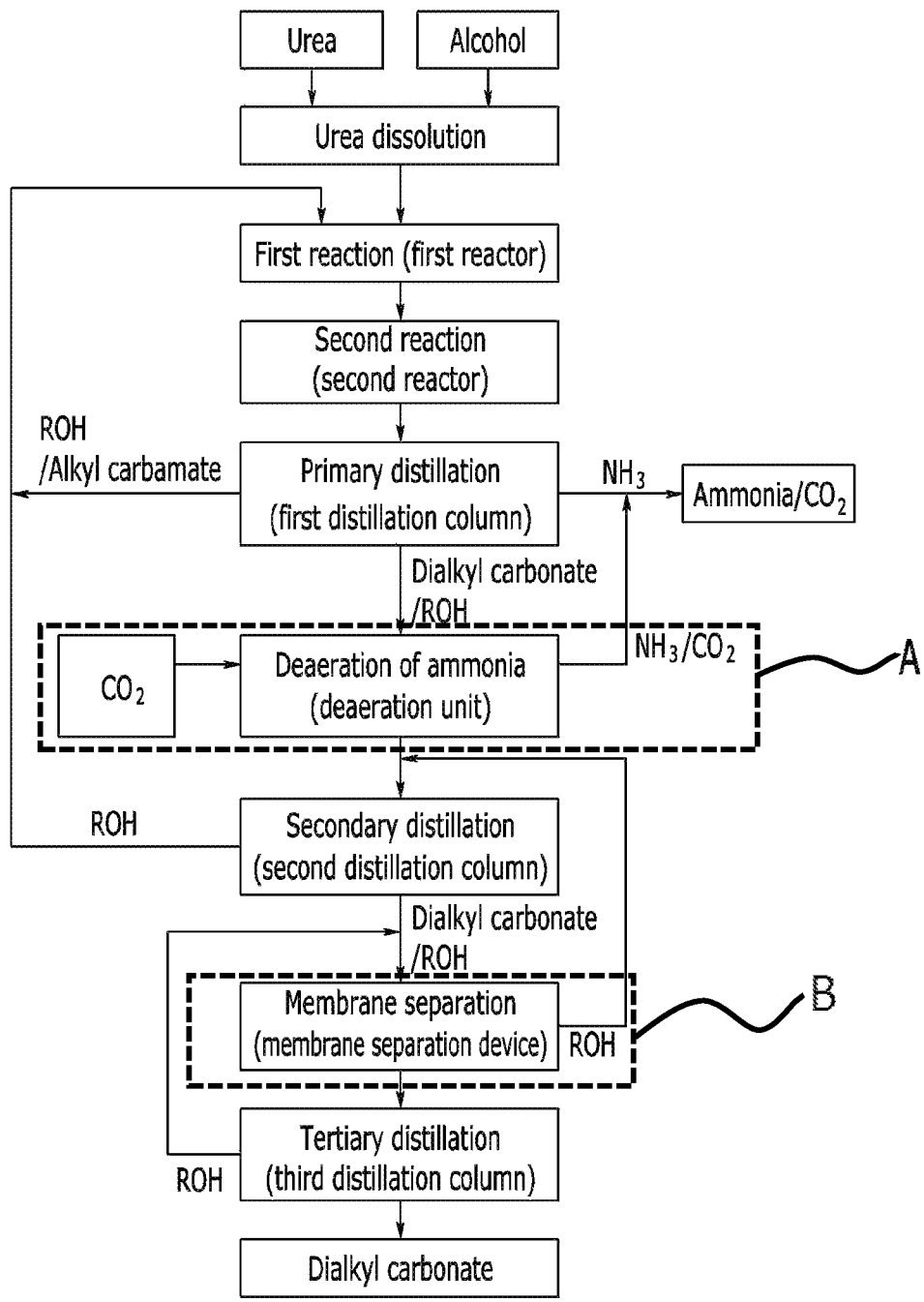
FIG. 2 is a flowchart schematically showing an example of a method for continuously preparing a dialkyl carbonate according to the exemplary embodiment of the invention.

FIG. 2 shows a more specific example of the method for preparing the dialkyl carbonate, which includes the separation step and/or the circulation and reuse steps, as a schematic flowchart. Referring to FIG. 2, the preparation method of the exemplary embodiment may include, after the reaction step (e.g., first and second reaction steps) is carried out, primarily distilling the product of the reaction in a first distillation column to circulate the unreacted residue of a column bottom into the reaction and purifying the by-product at a column top to form a product including ammonia, monovalent alcohol, and dialkyl carbonate, secondarily distilling in a second distillation column to circulate the unreacted residue of the column bottom into the reaction and form a product including monovalent alcohol and dialkyl carbonate at the column top, and tertiarily distilling in a third distillation column to recover a final product including dialkyl carbonate at the column bottom.

Hereinafter, a more specific example of the continuous preparation method and a preparation device for carrying out the method will be described for each step.

First, in the primary distillation step carried out immediately after the reaction step, the product of the reaction step may be distilled in the first distillation column. As a result of the primary distillation, the first product including dialkyl carbonate, for example, the mixture solution of dialkyl carbonate/alcohol may be generated together with the by-product including ammonia at the column top of the first distillation column.

The first product may be directly delivered to a secondary distillation step. Occasionally, the first product may be first delivered to a by-product purification and removal step and then to the secondary distillation step. When the by-product purification and removal step is carried out, recovered ammonia from the by-product purification and removal step may be reacted with carbon dioxide to be converted into urea and reused in the reaction step, When a portion of the by-product is purified and removed, the mixture solution of dialkyl carbonate/alcohol may be generated. The concentration of dialkyl carbonate of the mixture solution may be about 5 to 30 wt %. Further, ammonia may partially remain in the mixture solution.

As described above, in order to purify and remove a portion of the by-product including ammonia from the product of the column top, the cooler may be used, and ammonia may be separated and removed in a gas phase therethrough. In this case, the temperature of the cooler may be, for example, about 0 to 35° C. when methanol is used as alcohol. When the temperature of the cooler is excessively low, the amount of alcohol discharged in a vapor phase together with ammonia may be reduced. However, ammonia and methylamines as the by-product may be dissolved in the distillate, and thus a high cost and a lot of time may be consumed to recover ammonia and purify the by-product. On the contrary, when the temperature of the cooler is excessively high, a recovery ratio of methanol may be reduced. Therefore, the temperature of the cooler may be appropriately set in consideration of an economic aspect or a type of alcohol.

Meanwhile, the unreacted residue including alcohol and alkyl carbamate is separated at the column bottom of the first distillation column. The unreacted residue may be circulated into the reaction step, for example, the reactor for the first reaction step, and reused. In this case, a reflux ratio of the first distillation column may be about 2 to 24:1. An optimum yield of dialkyl carbonate may be obtained by refluxing alcohol at this reflux ratio. However, an appropriate reflux ratio may depend on the condition of the first distillation column and the distillate.

Further, it is appropriate that the temperature of the reboiler of the first distillation column be maintained in order to reflux the unreacted residue. In order to further efficiently reflux alcohol, it is preferable that a temperature conforming to the boiling point thereof, for example, a temperature of about 65 to 68° C. in the case of methanol, be maintained.

Meanwhile, after the primary distillation step is carried out, the second product including the monovalent alcohol and dialkyl carbonate is formed by deaerating and purifying ammonia remaining in the first product. Through the aforementioned step, ammonia remaining after being partially removed in the primary distillation step may be substantially completely removed. To this end, in the aforementioned step, ammonia may be removed by a method for stripping ammonia from the first product using carbon dioxide or nitrogen gas. In addition, remaining ammonia may be removed by various methods apparent to a person of ordinary skill in the art.

After the second product including alcohol and dialkyl carbonate is formed by deaerating and purifying remaining ammonia as described above, the second product may be secondarily distilled. When the secondary distillation is carried out, the unreacted residue such as alcohol is generated at the column bottom. The third product including remaining alcohol and dialkyl carbonate may be formed at the column top. In the third product, the unreacted residue such as alcohol may be circulated in the reaction step, for example, in the reactor for the first reaction step, and reused. The third product may be further purified through the subsequent step.

In the secondary distillation step, the second product may be subjected to azeotropic distillation. Through this, the third product formed at the column top of the second distillation column may be an azeotropic mixture of alcohol/dialkyl carbonate (e.g., in the case of the process for preparing dimethyl carbonate, the azeotropic mixture of 30 wt % dimethyl carbonate/70 wt % methanol at atmospheric pressure), and the unreacted residue such as remaining alcohol may be formed at the column bottom and concentrated. Concentrated alcohol may be circulated into the reaction step and reused.

Meanwhile, as described above, the unreacted residue generated in the first and second distillation columns may be circulated into the reaction step, for example, the first reaction step, and reused. When each reactant and the unreacted residue circulated in the first and second distillation columns are slowly injected into the reactor for carrying out the first reaction step, the productivity may be reduced. On the contrary, when the reactant and the unreacted residue are excessively rapidly injected, the productivity is increased. However, it may be difficult to control the reaction temperature due to vaporization heat of alcohol, and the concentration of dialkyl carbonate may be reduced due to an increase in unreacted alcohol. As a result, a purification cost of dialkyl carbonate, for example, a recovery cost of alcohol in each distillation step after the reaction step, may be increased, which is not preferable in view of an economic aspect. In consideration of the aforementioned matters, it is appropriate that alcohol of the unreacted residue circulated in the first and second distillation columns be added to alcohol supplied as the reactant and circulated and supplied to the reactor for the first reaction step so that the molar ratio of urea, alkyl carbamate, or the mixture thereof to alcohol included in the reactant is about 1:1 to 1:100, about 1:10 to 1:50, about 1:15 to 1:45, or about 1:15 to 1:40.

After the secondary distillation step is carried out, the third product formed therefrom may be subjected to membrane separation in the membrane separation device to further separate the unreacted residue such as alcohol. The further separated alcohol may be circulated into the second distillation column and reused.

Through the membrane separation step, an azeotropic point of the third product as the azeotropic mixture formed in the second distillation step may be broken, and through this, the fourth product including dialkyl carbonate may be formed at a higher concentration. In order to break the azeotropic point, a pervaporation device may be appropriately applied as the membrane separation device.

In addition, after the membrane separation step is carried out, the fourth product may be tertiarily distilled in the third distillation column. In the tertiary distillation step, the distillate of the azeotropic mixture of alcohol and dialkyl carbonate may be generated at the column top due to azeotropy. The distillate of alcohol may be circulated into the membrane separation device and reused. Further, the final product including the dialkyl carbonate may be formed at the column bottom of the third distillation column. The final product includes dialkyl carbonate with very high purity and thus may be recovered to finally obtain dialkyl carbonate having the high yield and purity.

Meanwhile, the device used to continuously prepare the dialkyl carbonate (e.g., dimethyl carbonate) according to the aforementioned method may have the following constitution. Referring to FIG. 2 and the continuous preparation method, the preparation device may include: a first reactor where the first reaction step of urea, the alkyl carbamate having 1 to 3 carbon atoms, or the mixture thereof with the monovalent alcohol having 1 to 3 carbon atoms is carried out in the presence of the room temperature ionic liquid and the catalyst; a second reactor of further reacting the product of the first reaction step to convert the isocyanic acid included in the product of the first reaction step into alkyl carbamate; the first distillation column connected to the second reactor to carry out the primary distillation step; a deaeration unit connected to an upper portion of the first distillation column to carry out deaeration and purification steps of ammonia; the second distillation column connected to the deaeration unit to carry out the secondary distillation step; the membrane separation device connected to an upper portion of the second distillation column to carry out the membrane separation step; and the third distillation column connected to the membrane separation device to carry out the tertiary distillation step. In the preparation device, the first, second, and third distillation columns may be the atmospheric distillation column. The membrane separation device may be the pervaporation device.

Optionally, the deaeration unit A as shown in FIG. 2 may be omitted and then the second distillation column may be directly connected to the first distillation column. Also, the ammonia recovered from the first distillation column may be reacted with carbon dioxide to be converted into urea. Also, when the membrane separation device B as shown in FIG. 2 is omitted, the first and second distillation columns may be the atmospheric distillation column and the third distillation column may be a high pressure distillation column with 11~15 atm to improve separation efficiency. In the preparation device, since each reaction or purification step carried out in the first, second, and third distillation columns, the deaeration unit, and the membrane separation device are previously described, a repeated description thereof will be omitted.

As previously described above, in the preparation device, dialkyl carbonate may be prepared at the high yield and reaction speed through the first and second reaction steps. The dialkyl carbonate having high purity may be efficiently obtained through the subsequent distillation step, membrane separation step, and deaeration step. Further, in each preparation process, generation of the by-product and the sub-reactant may be minimized and the reuse ratio of the unreacted residue may be increased. Therefore, dialkyl carbonate may be further economically prepared in a further environmentally friendly manner.

Hereinafter, operations and effects of the invention will be described in more detail through specific examples of the invention. However, the examples are set forth to illustrate the invention, and the scope of the invention is not limited by the examples.

Example 1

The reaction system was constituted by the reactor, the condenser, the stirrer, and the metering pump capable of injecting a predetermined amount of alcohol. The temperature of the condenser was maintained at 5° C. to secure vaporized products in a liquid state.

100 g of the ionic liquid [Choline][NTf$_2$], 2 g of the catalyst ZrO(NO$_3$)$_2$, and 7.5 g of urea were put into the reactor and stirred. After stirring for 30 min, heating was performed to 180° C. which was the reaction temperature, and methanol was then injected at a flow rate of 0.5 mL/min. In this case, the amount of injected methanol was 60 g. When injection of methanol was finished, the condensed product was re-circulated into the reactor at the same flow rate by the metering pump. The aforementioned procedure was performed at atmospheric pressure, the product was collected every 2.5 hours to measure the yield of dimethyl carbonate, and the aforementioned procedure was repeated after reaction for 12.5 hours. The yield of dimethyl carbonate at 12.5 hours was 46.2%, 53.9%, and 55.6% according to the number of repeated experiments, and a stable synthetic yield was obtained.

Comparative Example 1

The same procedure as Example 1 was performed to prepare dimethyl carbonate, except that 2 g of ZnO as a metal oxide was used as the catalyst instead of 2 g of ZrO(NO$_3$)$_2$. The yield of dimethyl carbonate at 12.5 hours was 40.0%, 47.2%, and 34.7% according to the number of repeated experiments, and the yield was reduced in the thirdly repeated experiment. Through this, unlike the case of Example 1, when the metal oxide catalyst was used, it could be seen that activity of the catalyst was reduced, and it was confirmed that the lifespan and activity were poor as compared to the catalyst of the metal salt of Example 1.

Example 2

The same procedure as Example 1 was performed to prepare dimethyl carbonate, except that 1.4 g of Ce(NO$_3$)$_3$ and 0.6 g of ZrO(NO$_3$)$_2$ were used as the catalyst instead of 2 g of ZrO(NO$_3$)$_2$. After the experiment was repeated three times, the yield of dimethyl carbonate at the reaction time of 12.5 hours was 43.0%.

Example 3

The same procedure as Example 1 was performed to prepare dimethyl carbonate, except that 2 g of Ce(NO$_3$)$_3$ was used as the catalyst instead of 2 g of ZrO(NO$_3$)$_2$. After the experiment was repeated three times, the yield of dimethyl carbonate at the reaction time of 12.5 hours was 36.3%.

Example 4

The same procedure as Example 1 was performed to prepare dimethyl carbonate, except that 2 g of La(NO$_3$)$_3$ was used as the catalyst instead of 2 g of ZrO(NO$_3$)$_2$. After the experiment was repeated three times, the yield of dimethyl carbonate at the reaction time of 12.5 hours was 43.0%.

Example 5

The same procedure as Example 1 was performed to prepare dimethyl carbonate, except that the ionic liquid [Choline][NTf$_2$] was used in an amount of 20 g that was smaller than 100 g (weight ratio of ionic liquid/catalyst=10). After the experiment was repeated three times, the yield of dimethyl carbonate at the reaction time of 12.5 hours was 48.3%.

Example 6

The same procedure as Example 1 was performed to prepare dimethyl carbonate, except that the ionic liquid [Choline][NTf$_2$] was used in an amount of 10 g that was smaller than 100 g (weight ratio of ionic liquid/catalyst=5). After the experiment was repeated three times, the yield of dimethyl carbonate at the reaction time of 12.5 hours was 44.3%.

In the examples and the comparative examples, the yield of dialkyl carbonate was measured by collecting samples after each reaction time and performing gas chromatography analysis (analysis condition: DB-WAX capillary column (0.25 mm$\phi$×30 m×0.25 µm), FID detector). The quantitative analysis of generated dimethyl carbonate was calculated by drawing a calibration curve using heptanol and analyzing the calibration curve, was applied to the following Math Figure 1 to calculate the yield, and measurement results of the yield of each example and comparative example are described in the following Tables 1 to 3.

Yield (%)=Amount of dialkyl carbonate (mol)/
    Amount of added raw materials (mol)×100    <Math Figure 1>

TABLE 1

| Classi-fication | Catalyst | Number of reactions | Yield of dimethyl carbonate according to reaction time (%) | | | | |
|---|---|---|---|---|---|---|---|
| | | | 2.5 hours | 5 hours | 7.5 hours | 10 hours | 12.5 hours |
| Example 1 | ZrONO$_{32}$ | 1 | 19.1 | 28.9 | 40.4 | 45.3 | 46.2 |
| | | 2 | 22.4 | 32.3 | 41.7 | 48.9 | 53.9 |
| | | 3 | 25.3 | 35.8 | 43.4 | 47.3 | 55.6 |
| Comparative Example 1 | ZnO | 1 | 25.1 | 40.0 | 42.0 | 41.2 | 40.0 |
| | | 2 | 23.2 | 29.3 | 43.3 | 47.1 | 47.2 |
| | | 3 | 17.6 | 24.7 | 28.9 | 33.0 | 34.7 |

TABLE 2

| Classification | Catalyst | Yield of dimethyl carbonate according to reaction time after experiment repeated three times (%) | | | | |
|---|---|---|---|---|---|---|
| | | 2.5 hours | 5 hours | 7.5 hours | 10 hours | 12.5 hours |
| Example 2 | ZrONO$_{32}$ + CeNO$_{33}$ | 17.4 | 25.8 | 32.7 | 40.0 | 43.0 |
| Example 3 | CeNO$_{33}$ | 17.1 | 24.0 | 30.2 | 35.5 | 36.3 |
| Example 4 | LaNO$_{33}$ | 22.2 | 30.0 | 34.3 | 41.0 | 43.0 |

TABLE 3

| Classification | Weight ratio of ionic liquid/catalyst | Yield of dimethyl carbonate according to reaction time after experiment repeated three times (%) | | | | |
|---|---|---|---|---|---|---|
| | | 2.5 hours | 5 hours | 7.5 hours | 10 hours | 12.5 hours |
| Example 5 | 10 | 27.6 | 35.4 | 40.0 | 44.2 | 48.3 |
| Example 6 | 5 | 17.2 | 31.8 | 40.4 | 41.9 | 44.3 |

*Continuous process experimental device for preparing dialkyl carbonate

In the following examples, a dialkyl carbonate such as dimethyl carbonate was prepared by using the device for continuously preparing dialkyl carbonate, which was described in the specification. In this case, a stirred reactor made of glass was used as the first reactor of the device for preparing dialkyl carbonate. The first reactor included a 1/16"φ Teflon tube for injecting the raw material thereinto to sufficiently immerse the raw material in the room temperature ionic liquid. Further, a 4-blade turbine type of stirrer and stirring motor were used in order to vaporize alcohol such as methanol at the reaction temperature and disperse the alcohol well. A heating mantle and a thermostat were provided in order to control the temperature of the reactor. A fixed-bed reactor (or auxiliary distillation column; second reactor) filled with the 5 mmφ×5 mm Raschig rings made of glass as the filler was provided, and the temperature control device was also provided at the upper portion of the first reactor. A nitrogen cylinder (N$_2$) was provided to substitute air in the first reactor. A metering pump and a digital scale for precisely measuring the supply amount were provided in order to supply the urea/alcohol (methanol) solution into the first reactor. Connection was performed so that refluxed alcohol (methanol) was supplied to the first reactor, and alcohol (methanol) was set to be vaporized in the first reactor through the Teflon tube.

In the first distillation column, two columns were provided and constituted by the lower distillation column (vacuum outer cover of 25 mmφ×350 mm) and the upper distillation column (vacuum outer cover of 12.7 mmφ)×610 mm). The upper and lower columns were provided so that the reactant generated from the second reactor and the vapor of unreacted alcohol (methanol) were injected into the center of the upper and lower columns to distill dialkyl carbonate such as dimethyl carbonate. The reboiler at the lower portion of the first distillation column was a three neck round flask having a volume of 250 ml, and a metering pump for refluxing the alcohol (methanol)/dialkyl carbamate (methyl carbamate) solution separated by the reboiler to the reactor and the liquid level controller for controlling a liquid level of the reboiler were provided while being linked with the alcohol (methanol) supply pump. Further, a digital scale capable of measuring the supply amount of alcohol (methanol) was provided, and a thermostat capable of controlling the temperature of the reboiler and the magnetic stirrer for preventing boiling were provided. Additionally, a reflux controller and a reflux valve were attached in order to control the reflux ratio, a differential pressure meter was provided in order to regularly check leakage of the alcohol (methanol) vapor and clogging of the inside of the device, and an absorption bottle for absorbing non-condensed ammonia from the upper portion of the cooler of the distillation column and a safety bottle for preventing backflow were provided to constitute the device for continuously preparing dialkyl carbonate.

Example 7

Figure 3:
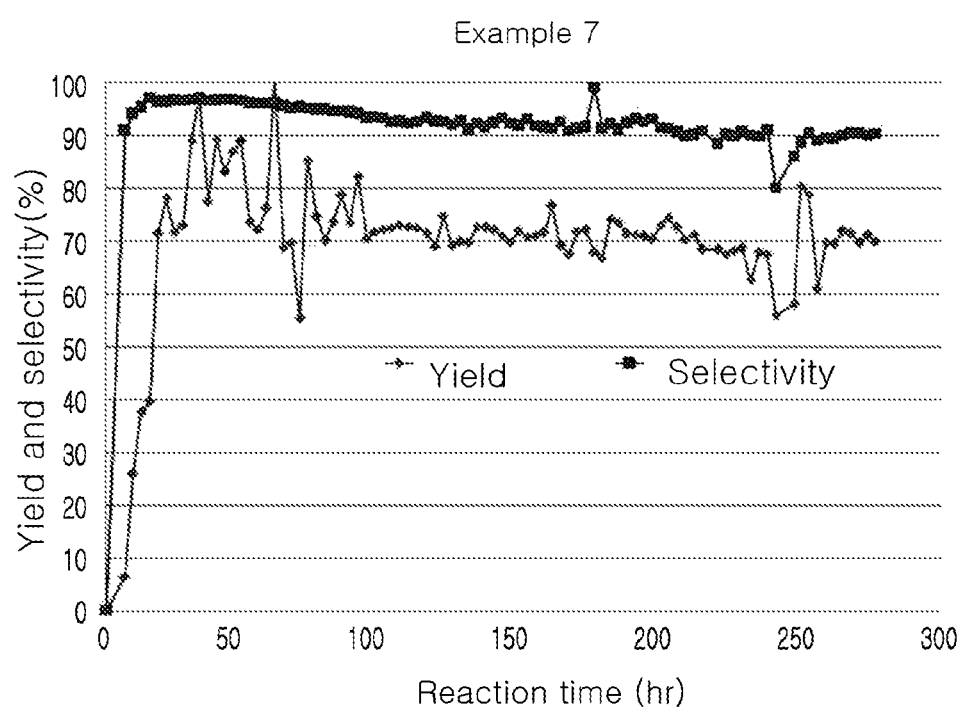
FIG. 3 is a graph obtained by measuring a yield and selectivity when dimethyl carbonate is prepared using urea as a raw material in an example.

Continuous Preparation of Dimethyl Carbonate 500 g of the [Choline][NTf2] room temperature ionic liquid was put into the 500 ml reactor by using the continuous process experimental device, 10 g of ZrO(NO$_3$)$_2$.6H$_2$O as the catalyst was dissolved, and when the reaction temperature reached 180° C., the urea/methanol solution was injected into the reactor through the metering pump at 0.5 ml/min so that the concentration of urea to methanol was 18 wt %. Further, unreacted methanol and methyl carbamate as the intermediate product in the reboiler of the distillation device were circulated into the reactor at a flow rate of 2.0 ml/min by using the pump to synthesize dimethyl carbonate. Subsequently, the mixture distillate of dimethyl carbonate and methanol was obtained from the upper condenser by using the distillation device at a reflux ratio of 1:12, and analyzed like in Experimental Example 2. The yield and selectivity are shown in FIG. 3.

Example 8

Continuous Preparation of Dimethyl Carbonate

Figure 4:
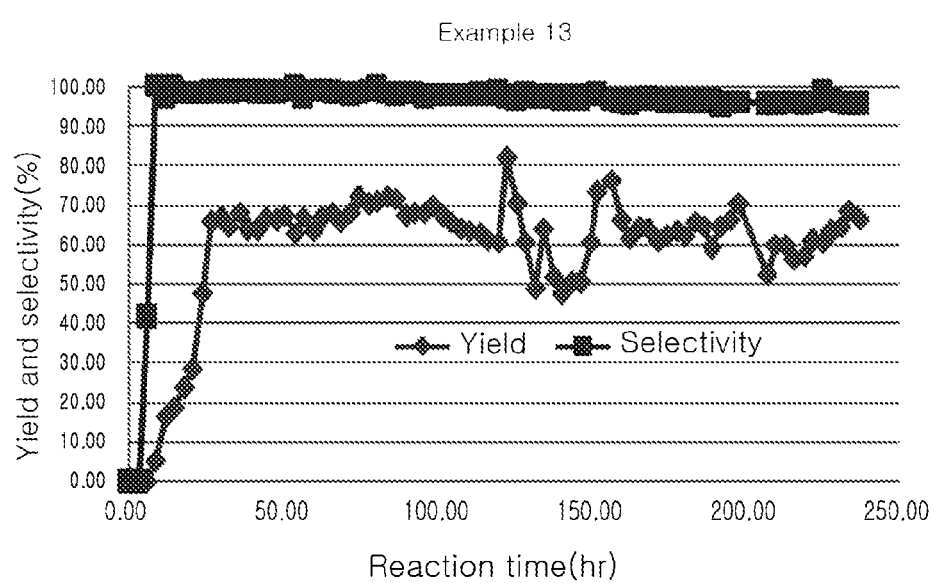
FIG. 4 is a graph obtained by measuring the yield and the selectivity when dimethyl carbonate is prepared using methyl carbamate as the raw material in the example.

The same procedure as Example 7 was performed to prepare dimethyl carbonate, except that methyl carbamate was dissolved in methanol at a concentration of 23.8 wt % and used as the raw material. The yield and selectivity were analyzed by the same method as Example 7, and are shown in FIG. 4.

Example 9

Preparation of Diethyl Carbonate

The same procedure as Example 1 was performed to prepare diethyl carbonate, except that 75 ml of ethyl alcohol was used instead of methanol of Example 1.

Example 10

Preparation of Di-n-Propyl Carbonate

The same procedure as Example 1 was performed to prepare di-n-propyl carbonate, except that 75 ml of n-propyl alcohol was used instead of methanol of Example 1.

Experimental Example 1

Analysis of Yield of Diethyl Carbonate and Di-n-Propyl Carbonate

In order to analyze the yields of diethyl carbonate and di-n-propyl carbonate prepared in Examples 9 and 10, the samples were collected when the reaction was performed for 2.5 hours, 6.5 hours, and 10.5 hours, and the gas chromatography analysis (analysis condition: DB-WAX capillary column (0.25 mmφ×30 m×0.25 μm), FID detector) was performed. The quantitative analysis of generated diethyl carbonate and di-n-propyl carbonate was calculated by forming the calibration curve using heptanol and analyzing the calibration curve, and applied to the following Math Figure 1 to calculate the yield. The results are described in the following Table 4.

Yield (%)=Amount of dialkyl carbonate (mol)/
Amount of added raw materials (mol)×100   <Math Figure 1>

TABLE 4

| | Yield of dialkyl carbonate (%) | | |
|---|---|---|---|
| | Reaction for 2.5 hours | Reaction for 6.5 hours | Reaction for 10.5 hours |
| Example 9 | 12.14 | 24.20 | 28.13 |
| Example 10 | 10.08 | 17.69 | 22.82 |

As described in Table 4, it can be seen that the yield is increased as the reaction time is increased. In the case of Example 9, the yield of diethyl carbonate was at most 28.13%, and the yield of di-n-propyl carbonate of Example 10 was at most 22.82%. Through this, it was confirmed that diethyl carbonate and di-n-propyl carbonate could be prepared at the high yield by the preparation methods of the examples.

Experimental Example 2

Analysis of Yield and Selectivity of Dimethyl Carbonate According to Raw Materials Continuous reaction was performed for 250 hours or more by using urea or methyl carbamate as the raw material in Examples 7 and 8. In order to analyze the yield and the selectivity of prepared dimethyl carbonate, gas chromatography analysis (analysis condition: DB-WAX capillary column (0.25 mmφ×30 m×0.25 μm), FID detector) was performed. After concentration and GC analyses of the distillate of dimethyl carbonate obtained by the first distillation, the analysis results were compared to those of the calibration curve to the peak area ratio to perform calculation. The calculated results were applied to Math Figure 1 and the following Math Figure 2 to calculate the yield and the selectivity, and the results are shown in the following FIGS. 3 and 4.

Selectivity (%)=Amount of dialkyl carbonate (mol)/
Total product (mol)×100   <Math Figure 2>

As shown in FIG. 3, when dimethyl carbonate was prepared by using urea as the raw material in Example 7, the selectivity exceeded 90% and the yield was about 70% or more on average for 250 hours. Trimethylamine and dimethylamine were generated as by-products other than dimethyl carbonate. The concentration of the by-products was at most 10% compared to the concentration of dimethyl carbonate, which meant selectivity of 90% or more.

Further, as shown in FIG. 4, when dimethyl carbonate was prepared by using methyl carbamate as the raw material in Example 8, the maximum yield was about 70%, the yield was about 65% on average for 250 hours, and the selectivity was maintained at 95% or more. Through this, it was confirmed that dialkyl carbonate could be prepared by using urea or alkyl carbamate as the raw material.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for preparing a dialkyl carbonate, comprising:
reacting urea, an alkyl carbamate having 1 to 3 carbon atoms, or a mixture thereof with a monovalent alcohol having 1 to 3 carbon atoms in the presence of a room temperature ionic liquid comprising a cation that is capable of generating a hydrogen ion ($H^+$) and a hydrophobic anion containing fluorine and a catalyst comprising a salt of a transition metal or a rare earth metal,
wherein the salt of the transition metal or the rare earth metal is a nitrate, a halide or a hydrate of the transition metal or the rare earth metal.

2. The method of claim 1, wherein the salt of the transition metal comprises a salt of a transition metal of Group III or IV.

3. The method of claim 1, wherein the catalyst comprises a salt of Zr, Ce, La, or Y.

4. The method of claim 1, wherein the catalyst comprises $ZrO(NO_3)_2$, $Ce(NO_3)_3$, $CeCl_3$, $ZrCl_4$, $La(NO_3)_3$, or $LaCl_3$, or a hydrate thereof.

5. The method of claim 1, wherein the cation is a quaternary ammonium-based cation, an imidazolium-based cation, a N-hydroxyalkylpyridium-based cation, a pyrazolium-based cation, a pyrrolinium-based cation, a quaternary phosphonium-based cation, a thiazolium-based cation, or a sulfonium-based cation having an alkyl group or a hydroxyalkyl group, and
the anion is a bis(trifluoromethylsulfonyl)imide anion, a trifluoromethanesulfonate anion, or a tris(trifluoromethylsulfonyl)methanide anion.

6. The method of claim 5, wherein the room temperature ionic liquid is [Choline] [$NTf_2$].

7. The method of claim 1, wherein the reaction is carried out at a temperature of 130 to 300° C. and a pressure of 0.1 to 15 atm.

8. The method of claim 1, wherein the urea, the alkyl carbamate, or the mixture thereof, and the monovalent alcohol, are used at a molar ratio of 1:1 to 1:100.

9. The method of claim 1, wherein the catalyst and the room temperature ionic liquid are used at a weight ratio of 1:1 to 1:1000.

10. The method of claim 1, wherein the reaction of the urea, the alkyl carbamate, or the mixture thereof with the monovalent alcohol comprises:
a first reaction of reacting the urea, the alkyl carbamate having 1 to 3 carbon atoms, or the mixture thereof with the monovalent alcohol having 1 to 3 carbon atoms in the presence of the room temperature ionic liquid and the catalyst; and
a second reaction of further reacting a product of the first reaction to convert isocyanic acid included in the product of the first reaction into alkyl carbamate.

11. The method of claim 10, wherein the first reaction is carried out in a stirred reactor, and the second reaction is carried out in a fixed-bed reactor.

12. The method of claim 11, wherein the fixed-bed reactor is filled with Raschig rings or a formed body in which a metal oxide catalyst is impregnated.

13. The method of claim 10, wherein the second reaction is carried out with addition of the catalyst comprising oxides of one or more metals selected from the group consisting of Zr, Ce, Zn, Ti, Pb, and Mg.

14. The method of claim 1, further comprising
after the reaction of the urea, the alkyl carbamate, or the mixture thereof with the monovalent alcohol,
separating a resultant product of such reaction from a product comprising dialkyl carbonate, a by-product comprising ammonia, and an unreacted residue comprising monovalent alcohol and alkyl carbamate.

15. The method of claim 14, wherein the unreacted residue comprising monovalent alcohol and alkyl carbamate is circulated into the reaction and reused.

16. The method of claim 1, further comprising,
after the reaction of the urea,
the alkyl carbamate, or the mixture thereof with the monovalent alcohol,
distilling a resultant product of such reaction in a first distillation column to circulate an unreacted residue of a column bottom into the reaction and purifying a by-product at a column top to form a first product comprising ammonia, monovalent alcohol, and dialkyl carbonate;
distilling the first product in a second distillation column to circulate the unreacted residue of the column bottom into the reaction and form a second product comprising monovalent alcohol and dialkyl carbonate at the column top; and
distilling the second product in a third distillation column to recover a final product including dialkyl carbonate at the column bottom.

17. The method of claim 16, further comprising
before distilling the second product in the third distillation column,
membrane separating the second product comprising monovalent alcohol and dialkyl carbonate in a membrane separation device to further separate the unreacted residue to circulate the unreacted residue into the second distillation column and form a product including dialkyl carbonate at a concentration that is higher than the concentration of the second product in the secondarily distilling step, and
wherein the first, second, and third distillation columns are atmospheric distillation columns, and the membrane separation device is a pervaporation device.

18. The method of claim 16, wherein the first and the second distillation columns are atmospheric distillation columns, and the third distillation column is a high pressure distillation column.

* * * * *